United States Patent [19]

Chaussy et al.

[11] Patent Number: 4,705,026

[45] Date of Patent: Nov. 10, 1987

[54] COAXIAL LOCATION FOR CONTACT FREE COMMINUTION OF CONCREMENTS

[75] Inventors: Christian Chaussy, Los Angeles, Calif.; Wolfgang Hepp, Immenstaad, Fed. Rep. of Germany; Dick van Rijn, Eriskirch, Fed. Rep. of Germany; Bernd Forssmann, Friedrichshafen, Fed. Rep. of Germany

[73] Assignee: Dornier System GmbH, Friedrichshafen, Fed. Rep. of Germany

[21] Appl. No.: 732,364

[22] Filed: May 8, 1985

[30] Foreign Application Priority Data

May 15, 1984 [DE] Fed. Rep. of Germany ....... 3417985

[51] Int. Cl.$^4$ .............................................. A61N 1/00
[52] U.S. Cl. ................... 128/24 A; 128/328; 378/177
[58] Field of Search .......... 128/24 A, 33, 303 B, 128/660, 328; 378/177, 180

[56] References Cited

U.S. PATENT DOCUMENTS

| | | | |
|---|---|---|---|
| 4,094,306 | 6/1978 | Kossoff | 128/24 A |
| 4,230,129 | 10/1980 | LeVeen | 128/804 |
| 4,526,168 | 7/1985 | Hassler et al. | 128/24 A |
| 4,539,989 | 9/1985 | Fossmann et al. | 128/328 |
| 4,610,249 | 9/1986 | Makotski et al. | 128/328 |

OTHER PUBLICATIONS

Dornier Kidney Lithotripter, By Dr. Ch. Chaussy et al., 20 pp., Institute for Surgical Research of the Ludwig-Maximilians Universitat Grobhadern Clinic (Director: Prof: Dr. Dr. h. c. W. Brendel) Date not known.
Extracorporeal Shock Wave Lithotripsy, by Chaussy et al., published 1982 (5 pp.).

Primary Examiner—Carroll B. Dority, Jr.
Attorney, Agent, or Firm—Ralf H. Siegemund

[57] ABSTRACT

A concrement in a human body is located by an X-ray system establishing an axis through the concrement; ultrasonic equipment determines a depth coordinate value for the concrement on that axis, and a shock gyrator and focusing system is placed on that established axis for obtaining the comminution. A rest is provided for placing the body in the action zone, and for establishing a second axis in a coordinate system; the third axis is perpendicular to the latter and defines locally the direction of position change for the various types of equipment needed to carry out the aforementioned program.

18 Claims, 4 Drawing Figures

COAXIAL LOCATION FOR CONTACT FREE COMMINUTION OF CONCREMENTS

BACKGROUND OF THE INVENTION

The present invention relates to the contactless comminution of concrements in the body of a living being under utilization of shock waves using particularly a source in which shock waves are generated, a focusing reflector and a system or device for locating concrements in the body. Furthermore a rest for the patient is to be provided.

German Pat. No. 2,351,247 corresponding to U.S. Pat. No. 3,942,531 discloses a device for comminution of concrements in the body of a living being using a focusing chamber constructed as a portion of a rotational ellipsoid having two focal points; in one of the focal points shock waves are generated through spark discharge while the device as such is positioned with respect to the body of the living being so that the second focal point coincides with the previously located concrements such as a kidney stone. Such a device then permits the comminution of kidney stones in a non-invasive manner, not even requiring the insertion of probes.

The socalled kidney lithotripter made and installed since 1983 by Dornier System GmbH includes two X-ray imaging systems for localizing and pinpointing the location of a kidney stone basically by triangulation and ascertaining at the same time the size of that stone. The kidney lithotripter proper is then positioned and triggered and the focused shock waves comminute the kidney stone to obtain a rather fine grain grit, which will subsequently be discharged from the body in a natural manner.

The device for generating the shock waves, or field of shock waves, and the device or devices for locating the kidney stone are arranged so that they do not mutually interfere. Basically one uses two X-ray devices for stereoscopically locating the kidney stone and they are placed to both sides of the shock waves generator and reflector (see e.g. "Dornier Kidney Lithotripter"). The two central beams of the X-ray locating devices intersect the axis on which the two focal points are located, in each instance by about 40° and that intersection is of course to be right in the location of the kidney stone.

Since the kind of arrangement just described requires two separate X-ray devices it is rather expensive. Moreover, certain portions of the reflector structure have to be provided with cut-outs or the like, to permit passage of Xrays. Also a certain coupling fluid is required such as water, since from the point of generation to the point of action the shock waves should propogate through an accoustically homogeneous medium in order to avoid scatter or even unwanted ordered reflection with parasitic focussing in the wrong spot. Also, any attenuation of the shock waves is to be avoided as much as possible. The coupling water moreover is an impediment for X-rays and may require the introduction of inflatable bellows.

DESCRIPTION OF THE INVENTION

It is an object of the present invention to provide a new and improved method and equipment for contactless comminution of concrements in bodies of living beings in which the locating of these concrements in the body can be carried out in a less expensive manner and more efficient than was heretofore possible.

It is therefore a particular object of the present invention to provide for a new and improved contactless comminution of concrements in bodies of living beings under utilization of a shock wave source and generator, a focusing shock wave reflector, and locating device and equipment in a novel configuration and arrangement.

In accordance with the preferred embodiment of the present invention it is suggested to improve method and equipment in accordance with the particular object, by providing at least one equipment carrier in relation to a rest for the patient, or living being generally, for selectively placing it in a mutually exclusive manner the shock wave system including source and reflector, and at least one concrement locating system such as a single source of X-ray and X-ray image amplifier or a film or plate holding cassette and/or an ultrasonic imaging system.

Therefore it is an essential feature of the invention, to exchange the device or devices for locating and the device or devices for shock wave generation and focusing, whereby the equipment is constructed to be situated in relation to a common axis. This feature will then permit establishing with a single X-ray system the generation of the X Y coordinates of the concrement such as a kidney stone or a gall stone, whereby the common equipment axis is the Z axis of this coordinate system. In other words the system provides for reproducibly establishing a Z-axis which traverses the concrement using a single X-ray system, and the shock wave source is then placed on that axis.

It is feasible to make the X-ray path length within the body or the living being as well as within any water path as small as possible and practicable, whereby the above mentioned question of mutual interference of different types of equipment is no longer a problem. Therefore, the usual X-ray conditions for obtaining the customary AP (antero posterior) condition are maintained. Accordingly the requirement on the single X-ray locating system is reduced as compared with the known two X-ray device systems. The X-ray image amplifier or the photographic film are preferably placed as close to the location of the concrement; in the case of a kidney stone this is below the patient, in cases of gall stones the location is above the patient.

The Z coordinate value of the location of the concrement can also be described as a depth value and distance from the skin of the patient. This Z-value is either determined prior to the treatment f.ex. by separate ultrasonic measurement under comparable position of the patient. Alternatively, an ultrasonic sensor is integrated with the aforementioned equipment so that after having found the X and Y coordinates of the concrement, the Z coordinate is determined thereafter.

Locating the concrement by means of an ultrasonic sensor is considerably facilitated as compared with the more or less blind search conducted in the past because prior adjusting of the equipment on the given X Y coordinate system the concrement will automatically appear in the center of the ultrasonic system. If the X Y adjustment of the X-ray system is used in addition to ascertain any direction of movement of the concrement, f.ex. on account of breathing of the patient, then the ultrasonic imaging plane can be arranged parallel thereto, so that after the X-ray system has been exchanged for the ultrasonic depth measuring system, the stone will remain visible independently from any excursion on account of breathing by the patient.

The depth measurement of the stone, i.e. the acquisition of the Z coordinate may in some cases be dispensed with entirely or one may even provide an anatomic estimate so that instead of a point or spindle shaped focal point one may use a short line focus having a noticeable extension along the Z axis.

The invention can be practiced in an environment wherein a pan or tub is used for providing accoustic coupling between the body of the patient and the focusing device. But the invention can also be practiced where there is no such tub or pan, but the shock wave generator and focusing device is water coupled to the patient in a location geometrically close to the respective concrement.

The exchange or switchover from the concrement locating system to shock wave generating system requires of course a precise position of the patient in an atomically optimum fashion, whereby particularly the equipment carrier and the patient should not move in relation to each other. This presents some problems, because the exchange of the overall system components particularly if there is no tub, cannot be carried out without somehow touching the patient. But still there must be no movement. Therefore it is suggested, in addition, to provide certain pans or shells having a relatively large area for receiving, so to speak, the patient; not merely in terms of support, i.e. to be effective, generally vertically against gravity, but also laterally so that the patient as a whole, particularly his or her torso, will not move laterally.

These contoured pans or shells and related support means may be constructed of a passive deformable medium f.ex. under utilization of a granulate confined in a low pressure container. This way the patient can be conveniently positioned, particularly laterally in a stable fashion whereby moreover the areal force, i.e. the pressure effective on the skin of the patient is as small as possible, particularly for avoiding that the blood circulation is not interfered with in any manner.

In a particular advantageous configuration, it is suggested to provide the system for generating and focusing shock waves and the locating system on sliding carriages respectively above and below the patient and to make them, i.e. the slideable carriages, slideable in a direction generally, perpendicular to the axis of the body of the patient and to provide in addition for latched positioning of these slide carriages to thereby adjust and hold the positions of the locating and shock wave generating and focusing system.

In lieu of linearly moveable, slidelike or wheeled vehiclelike carriages one can use an arrangement of equipment carrier which is of drum or revolver like configuration. Therefore the exchange in position of equipment is the result of a turning motion. Still alternatively one may use here two rotating equipment carriers, one for the upper and one for the lower equipment. The axis of rotation could be either the general longitudinal axis of a resting patient or any axis perpendicular thereto. A mechanical or electrical coordination of the respective position can be provided in either case.

In furtherance of the invention, one can in the alternative provide a single arc shaped equipment carrier for all of the equipment which loops around the patient and again the axis of rotation may approximately at least coincide with the longitudinal axis of the resting patient.

For comminuting a concrement it is of advantage if the shock wave generating and conducting system generally, such as for example a focusing ellipsoid with water coupling path for depth compensation and including a coupling membrane, the X-ray source, and the ultrasonic sensor are all provided on a carriage arranged underneath the patient and being moveable transversely to the general longitudinal direction of extension of the resting patient whereby the carriage is positionable in several particular well defined working positions. The X-ray image amplifier or the cassette holding the X-ray film and a coupling cushion, in case there is no tub or pan, possibly also another ultrasonic sensor are arranged on a slide carriage generally above the patient and that slide is likewise moveable transversely to the longitudinal axis of the patient in a resting position, whereby the two carriages should move in a coordinated fashion. In the case of revolving equipment carriers, the orientation is an analogous one.

For purposes of kidney stone communition, the X-ray image amplifier should be placeable as close to the kidneys as possible, which in effect means that this device should be arranged underneath the patient, assuming that the patient rests on his back. Adjusting the patient himself relative to the ellipsoid in the direction of extension of the body which is the X-direction for example, as well as adjusting the patient in height which is the Z direction can be provided advantageously through shifting the rest on which the patient lies, while the adjustment in the Y direction, being of course transversely to both the X and Z direction, occurs through shifting of the latch position of the upper and lower equipment carriages.

Equipment carriages above and below the patient each have devices for latching in definite positions, f.ex. in three different operating positions. The latching should be provided by means of latches, claws or the like, which latch in a play free fashion. In order to obtain lateral positioning (Y direction) the latch housing and therefore the carriage itself can be shifted in lateral direction. This means that the X-ray and the application azis are shifted laterally in parallel but they remain associated to each other as before. The slide or wheeled vehiclelike carriage for the various pieces of equipment as stated are generally of course useable irrespective of whether or not a tub is used for partially submerging the patient.

In the case of a tub the bottom of the tub is of course very close to the kidney of the patient and here it is suggested to provide a window in the tub bottom being permeable to X-rays as well as to acoustic shock waves. This window will not in effect be in physical contact with the patient. The window may be configured as a polyurethane toil being about half a millimeter thick. Upon coupling the shock wave equipment with water coupling path to that window one ensures that the pressure in the bellow system of that coupling path is below the hydrostatic pressure in the bottom of the pan. This can be attained through a simple pressure dividing system which controls the bellows pressure in accordance with a hydrostatic pressure as it prevails near the bottom of the tub. This feature avoids bulging of the membrane in an up direction. Such bulging could in some form shift the patient. The same method and aspects can be practiced even if no tub is used but, one uses a thin water cushion instead for further coupling.

In lieu of a point like, true focal point of the ellipsoidal reflector one should use an axial line focus in order to produce a laterally tightly limited but intensified shock wavefront held together over a finite line portion. The effective zone is enhanced by such modified focusing of the shock wave which means that the locating procedure is less critical and therefore does not have to be as accurate as was previously deemed necessary. Widening the focus transversely to the direction of propagation of the shock wave for equal pressure amplitude in the focus would require increasing the shock wave energy in proportion to the frontal area which of course would mean that the electrodes as well as the patient are loaded with ultrasonic energy to an increasing extent. In case of too low a pressure amplitude the dynamic duration strength of the material of the concrement would not be reached and therefore the stone would not be destroyed.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
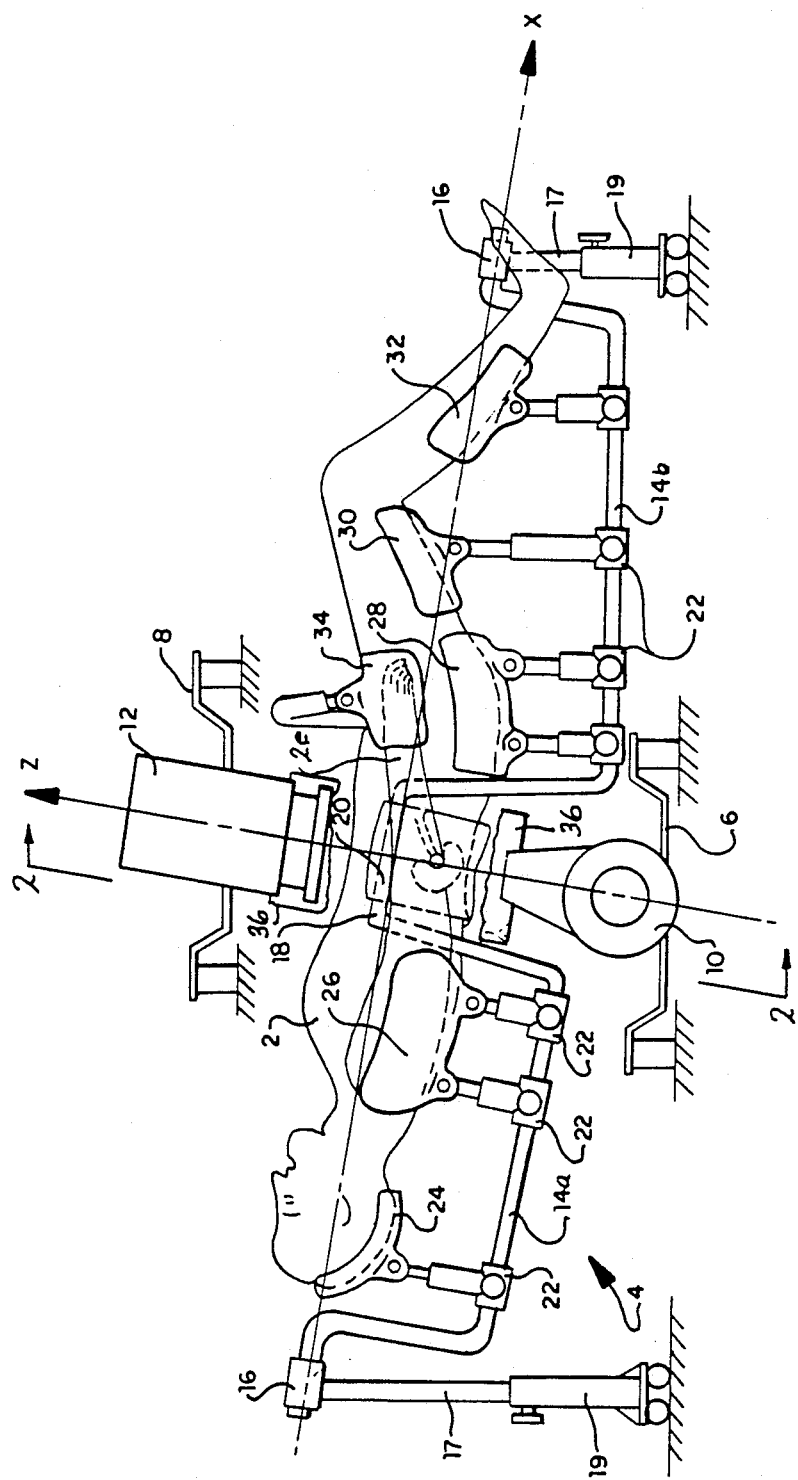
FIG. 1 is a side view of a preferred embodiment of the present invention for practicing the best mode thereof.

Proceeding now to the detailed description of the drawings reference is made to FIG. 1 which illustrates in effect a side view of the equipment taken in the x,z plane, the coordinate directions x and z are indicated accordingly. The figure shows in particular a patient 2 resting on a rest 4 of complex configuration. There is also shown an equipment carrier constructed as a slide carriage 6 and being situated underneath the patient 2. A second equipment carrier also constructed as a slide carriage 8 is shown to be positioned above the patient 2. The carriages 6 and 8 run on suitably positioned stationary rail beds. These beds are offset corresponding to the inclination of axis Z to the vertical and of axis X to the horizontal. The offset or rail beds may be adjustable in order to adjust that angle.

Generally speaking the carriages are provided for supporting structure for locating concrement and for producing, focusing, and conducting shock waves. Specifically the lower carriage 6 is movable along the Y axis and carries an X-ray tube 10 and the upper carriage 8 is also movable along that Y-axis and carries an X-ray amplifier 12 or X-ray sensitive plate holder. The carriages 6 and 8 are movable transversely to the plane of the drawing of FIG. 1, the Y direction is shown in FIG. 2.

The lower carriage and slide 6 holds, in addition to the X-ray tube 10, the shock wave generator and focusing structure 38 with coupler bellows 38a, and an ultrasonic pick-up and sensing device 40. An accoustic output coupling and positioning cushion 42 with bellows contesting the human body 2 and a second ultrasonic pick up and sensing device 44 are provided on the upper slide carriage 8 in addition to X-ray receiver 12.

Figure 2:
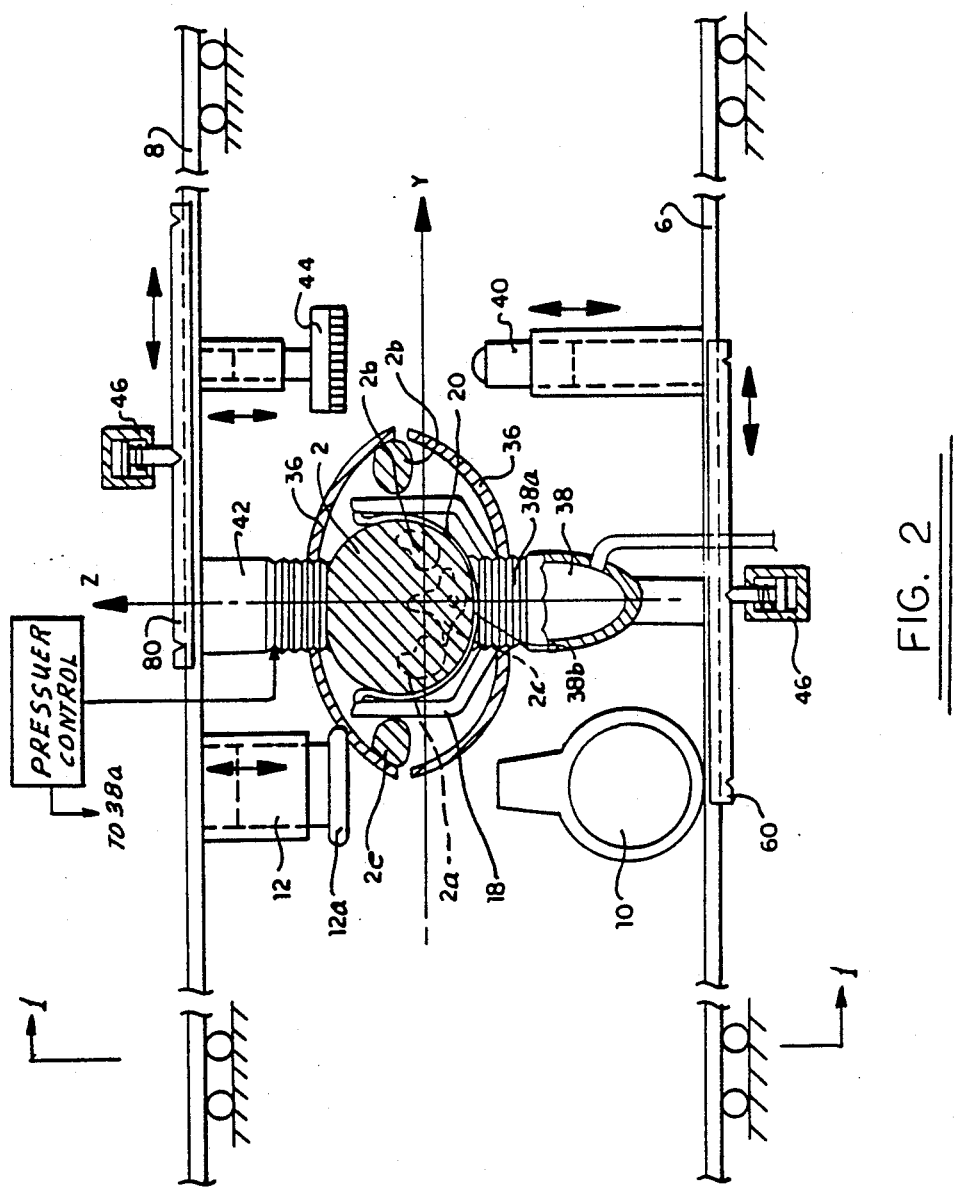
FIG. 2 is a cross-section through the embodiment of FIG. 1.

FIG. 2 illustrates the kidneys 2a and 2b of the patient 2; his back bone 2c, the liver 2d, and arms 2e. FIG. 2 shows also, that groups of equipment are aligned along parallel axes, each of which can be aligned with the Z-axis. Thus, X-ray source on carriage 6 is aligned with X-ray receiving equipment 12; the shockwave generating, focussing annd conducting equipment 38, 38a on 6 is aligned with the accoustic output couple 42 on 8 and the two ultrasonic devices 40 and 44 are aligned with each other. Shifting of the carriages 6 and 8 along the Y axis places selectively any of these three equipment alignment axis into coaxial relation with the Z-axis. This equipment does not mandate rigid coupling of the two carriages 6 and 8, though that is, of course a possiblity. It is sufficient that the equipment alignment as defined be an operative one, i.e. can be reestablished when needed. For this, latch positions are provided on the carriages cooperating with stationary play free latching elements or clamps 46. The latch positions are slidably established on the carriages by latch position carriers 60 and 80. Adjustment of these latch position carriers establishes the Y coordinate value for locating and positioning the several equipment pieces. The double arrows on equipment 40, 42 and 44 denote resilient suspension of the respective carriers.

The rest 4 is of modular construction whereby a high degree of commonality is observed. Parts with similar function should be configured as similar as is possible and this includes particularly the pans receiving limbs as well as the respective adjustment and positioning devices. Generally the rest is comprised of a tubular frame having an upper crimped portion 14a near the head and the upper torso, and a lower crimped portion 14b along the legs. These portions 14a and 14b are joined by bi-parted central tube frame 18.

Bearings 16 are provided in an aligned relationship and in fact now define the X-axis such that the patient can in fact be rotated about the x-axis which coincides as much as possible with the longitudinal axes of the patient when placed on the rest 4. This rotation is normally not permitted i.e. there is a break provided, not shown, which prevents the rest from rotating. Rotation is only permitted during particular manipulations and the rest can be held in a rotated position. These bearings are mounted on posts 17 which in turn are mounted on carriages 19. The carriages 19 permit adjustment of the position of the rest, basically along the X axis in relation to the equipment carrying carriages 6 and 8.

Figure 4:
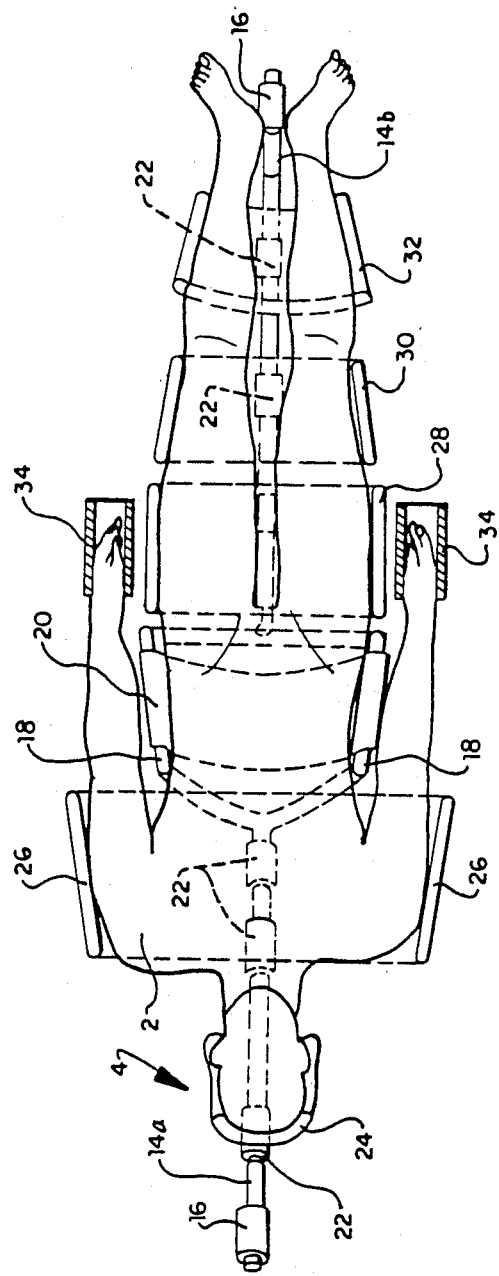
FIG. 4 is a top view of the rest for patient.

As stated, the central tube is bi-furcated to establish frame 18, in the area of application generally, that is the area traversed by X-rays, ultrasonic rays, shock waves etc (see also FIG. 4). The two portions 18 each are connected to the portions 14a and 14b, and each of the portions 18 are upwardly crimped towards the center of the patient.

The central portion 18 of the rest 4 as bi-furcated includes two pans 36 being comprised of active or passive heat tunnels which can be folded on top or slid onto the body of the patient or the torso of the patient. The intermediate space between the two central portions 18 is either individually adjusted or is the result of the tension of a carrier foil 20 which is suspended in the central area and is in fact permeable to X-rays as well as to shock waves. The particular contour of the foil is the result of the patient to and his/her wieght. The space between rod portions 18 defines the diagnostic/therapeutic application zone.

Cam elements 22 ride etc. on various rod or tube portions and carry anatomically suitably contoured carrier pans made for example of thermoplastic material or being configured as metal flat pans but lined with vacuum cushions filled with granular material, are articulated on these cams 22; their position can be arrested through suitable clamping features. In the particular embodiment there is a head pan 24, a back pan 26, a rump pan 28, leg upper (thigh) pans 30, and lower leg pans 32.

All these aspects are independent whether or not this entire configuration is placed into a tub or not; if so a certain hold down device 34 may be provided such as belts to tie the patient to the equipment in order to avoid buoyancy movement. Also, output coupler 42 and coupler bellows 38a are not needed in this case.

As stated the two slide carriage 8 and 6 may each assume one of three respective working and operating positions, and in these positions they can be latched by means of the playfree configured clamps 46 or the like. For different medical tasks and objectives one may include several reflectors and shock wave generators in order to accomodate the system for the comminution of both, kidney stones and gallstones. Also a certain differentiation has to be made in the treatment of children and adults. The carriages 6 and 8 are constructed in order to provide for this accomodation. The coupling path 38a of the shock wave generator/reflector 38 is configured stiff as far as its lateral portions are concerned so that tangential forces can be taken up which trangential forces arrive during lateral displacement and are transmitted through the coupling gel upon the coupling membrane. One may need in some cases additional guide elements in order to exercise a more positive control of whatever movement and displacement is produced.

The X-receiver 12 is if constructed as an image amplifier in this particular example, is provided with a pressure controlled air cushion 12a, disposed right at the front area of the image amplifier proper. The purpose of cushion 12a is that upon moving the amplifier towards the patient (along the Z-axis) and on contact with him or her this movement is to be precisely stopped at the point of contact so that the patient is not forced in down direction as a side effect of this adjusting motion of the image amplifier; as that would dislocate him or her. In other words if a full pressure force is exerted by the equipment on the patient during the locating procedure then upon relaxing, the position of parts of the patient may change and the locating measurements are no longer valid.

The ultrasonic sensing equipment 40 and 44 generally speaking is resiliently supported so as to automatically abut without an air gap against either the back or the stomach of the patient 2. A suitable couple gel paste may have been rubbed onto the skin of the patient in order to insure air gap free coupling.

The positioning and coupling cushions 42 are water filled and serve primarily for avoiding damage and injury to the patient particularly at the point of coupling ultrasonic energy out of the body. Moreover these cushions hold the body of the patient in the particular desired position. The water pressure inside positioning cushion 42 is preferably controlled analogously to the contact pressure of the coupling path 38a of the ellipsoidal reflector 38. This way one avoids also that the patient 2 is moved from the desired position. In view of an easier coupling and smaller entrance window one will preferably use sector scanners as the ultrasonic sensing device 40.

Figure 3:
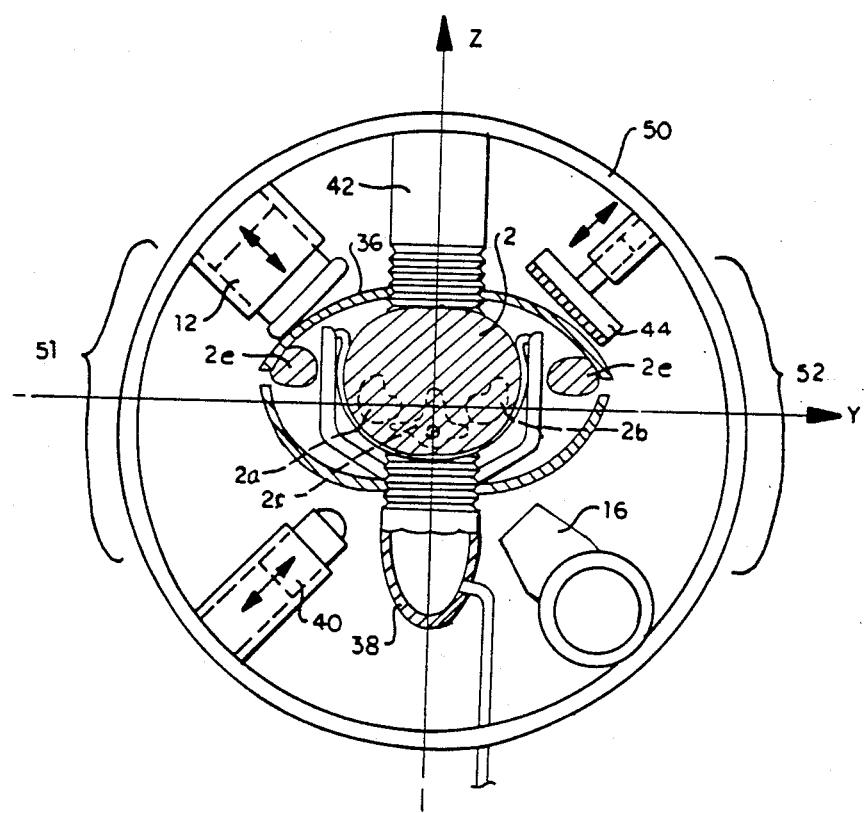
FIG. 3 is a modification showing rotatable equipment carrier.

Turning briefly to FIG. 3, a revolver or drum shaped equipment carrying system 50 is shown, including for instance a single circular carriage 50, carrying the equipment pieces 10, 12, 38, 42; 40 and 44 in radial alignment along the periphery, for rotation about the X axis, and for alignment of equipment pairs with the Z axis as afore described. It can be seen, that the bracketed carriage portions 51 and 52 are not really needed. Hence, the single carriage could be bi-parted, possibly for independent rotation of the arcuate parts.

In operation a patient is placed on rest 4 and the various pans 24, 26, 30 and 32 as well as sheet 20 are appropriately adjusted. The rest 4 is turned so that the kidney containing the stone to be comminuated is traversed by the Z axis. Next, the carriages 6 and 8 (or 50) are shifted into the position in which the X-ray equipment 10, 12 as aligned, is coaxially disposed on the Z axis. Centering on the kidney stone may require shifting the Z axis laterally e.g. through lateral adjustment of the stops 46 or of the rest 4 or of latch positioners on the carriages, i.e. the "notches" as a group being situated on the separate elements (60, 80) and to be shifted on the respective carriage. The rest 4 as a whole is shifted basically along the X axis by the carriage 19. After the kidney stone has been located and centered in the origin of the X Y Z coordinate system, the ultrasonic equipment 40 and 44 is aligned with the Z-axis and the depth (Z coordinate) of the stone is ascertained. Finally, the shock wave equipment 38, 42 on the carriage is aligned with the Z axis in immediate prepration for the ensueing comminution. The final adjustment involves spacing the focussing chamber 38 along the Z axis in accordance with the depth measurement. The bellows 38a adapt the coupling path length accordingly.

The invention is not limited to the embodiment described above, but all changes and modifications thereof not constituting departures from the spirit and scope of the invention are intended to be included.

We claim:

1. In a device for contactfree comminution of concrements in the body of a living being including a shock wave generating and reflecting system, at least one concrement locating system and a rest for said living being the improvement comprising:
   at least one equipment carrier for said shock wave system and said one or more locating systems; and
   means for displaceably supporting said equipment carrier for selective positioning said shock wave system or said one locating system in a particular position with respect to said rest to thereby obtain a particular position of either and both said shock wave system and said one locating system with respect to the rest and a body having been placed on said rest, so that the shockwave system can replace said locating system in said one particular position.

2. The improvement as in claim 1 there being a first equipment carrier and a second equipment carrier arranged with respect to said rest such that different pieces of equipment placed on the first and second carrier can be operationally coupled to each other along an axis that traverses the body of said living being when on said rest.

3. The improvement as in claim 2 wherein said first carrier carries at least one source of X-ray, the second carrier carrying an X-ray receiving device.

4. The improvement as in claim 1 said locating equipment including at least one ultrasonic imaging device.

5. The improvement as in claim 1 said rest including frame means and large area pans for providing support surfaces for parts of said living being and having lateral upward extensions for limiting lateral displacements of such parts.

6. The improvement as in claim 5 said pans including means for contour adapting to the contour of the parts of the body.

7. The improvement as in claim 1 said equipment carrier including a carriage said supporting means being provided for displacement of the carriage on the supporting means in the direction perpendicular to a longitudinal axis as defined by said rest in representation of position of the body on said rest, there being means for latching the carriage into particular operating positions.

8. The improvement as in claim 2 wherein one of said carriers is a carriage and holds X-ray receiving means and an accoustic coupling cushion, a second one of the carriers is also a carriage and holds an X-ray source, a shock wave generator and reflector, and an ultrasonic locating device.

9. The improvement as in claim 8 wherein said second carriage is generally below the rest and said first carriage above the rest.

10. The improvement as in claim 1 including a plurality of water cushions for positioning in abutment with said body so as to retain the body in a predetermined position.

11. The improvement as in claim 10 including pressure controlling means for said cushion.

12. The improvement as in claim 1, said carrier being of curved configuration.

13. The improvement as in claim 1, the locating system including pieces of equipment to be placed in physical contact with the living being, said pieces being resiliently mounted.

14. The improvement as in claim 1, including means for gapless contact making by at least one equipment piece on the carrier with the living being.

15. In a device for contactfree comminution of concrements in the body of a living being including a shock wave generating and reflecting system, at least one concrement locating system and a rest for said living being the improvement comprising:
    means for positioning the concrement locating system within an X-Y coordinate system, such that a third (Z) coordinate through the origin of the X-Y system runs through the concrement;
    means for measuring the Z-coordinate value of the concrement; and
    means for positioning the shock wave generating and reflecting system on said Z coordinate for being effective at a depth corresponding to the measured Z-coordinate value.

16. A method for contactless comminution of concrements in the body of a living being, comprising the steps of:
    locating a concrement by means of X-rays such that an axis for a beam of X-rays runs through the concrement;
    marking a representation of that axis such that subsequently other equipment can be located with respect to said axis;
    measuring a depth value for the concrement on the axis under utilization of the representation of the axis;
    positioning a shock wave generating and focussing device on said axis under utilization of the representation of the axis and under further utilization of said dept value as measured; and
    operating said device for comminution of the located concrement.

17. Method as in claim 16, said measuring step using ultrasonic depth measurement.

18. Method as in claim 16, wherein said locating, measuring and positioning steps are carried out with reference to a rest for said body.

* * * * *